United States Patent
Ways

(10) Patent No.: US 6,291,446 B1
(45) Date of Patent: Sep. 18, 2001

(54) THERAPEUTIC TREATMENT FOR CYTOMEGALOVIRUS INFECTION

(75) Inventor: Douglas Kirk Ways, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/253,700

(22) Filed: Feb. 22, 1999

Related U.S. Application Data

(60) Provisional application No. 60/076,857, filed on Mar. 5, 1998.

(51) Int. Cl.$^7$ .................... A61K 31/33; A61K 31/555
(52) U.S. Cl. ............................. 514/183; 514/185
(58) Field of Search ..................... 514/183, 185

(56) References Cited

U.S. PATENT DOCUMENTS

| | | | |
|---|---|---|---|
| 5,057,614 | 10/1991 | Davis et al. | 548/466 |
| 5,481,003 | 1/1996 | Gillig et al. | 548/455 |
| 5,491,242 | 2/1996 | Gillig et al. | 548/455 |
| 5,545,636 | 8/1996 | Heath, Jr. et al. | 514/214 |
| 5,552,396 * | 9/1996 | Heath, Jr. et al. | 514/183 |
| 5,559,228 | 9/1996 | Gillig et al. | 540/460 |
| 5,621,098 | 4/1997 | Heath, Jr. et al. | 540/472 |
| 5,710,145 | 1/1998 | Engel et al. | 514/183 |

FOREIGN PATENT DOCUMENTS

| | | | |
|---|---|---|---|
| 42 43 321 A | 6/1994 | (DE) | C07D/487/14 |
| 0 428 103 A | 5/1991 | (EP) | A61K/31/44 |
| 0 657 411 A1 | 6/1995 | (EP) | C07D/43/174 |
| 0 657 458 A1 | 6/1995 | (EP) | C07D/498/22 |

OTHER PUBLICATIONS

Slobbe–van Druneb et al, Virus Research, vol. 48(2), pp. 207–213, 1997.*

Wilkinson et al. "Isoenzyme specificity of bisindolylmaleimides, selective inhibitors of protein kinase C" Biochem J. (1993) 294 pp. 335–337.

Marlea E.P Slobbe–Van Drunen et al. "Activation of proten kinase C enhances the infection of endothelial cells by human cytomegalovirus" Virus Research, vol. 48, No. 2, 1997 pp. 207–213.

M.I. Hassan et al. "Involement of cAMP and protein kinase C in cytomegalovirus enhancement of human immunodeficiency virus replication" Proc. Soc Exp Biol Med., vol. 204, No. 2, 1993, pp. 216–223.

* cited by examiner

*Primary Examiner*—Russell Travers
(74) *Attorney, Agent, or Firm*—Paul R. Darkes

(57) ABSTRACT

A method for treating CMV infection and disease conditions associated therewith is disclosed, particularly using the isozyme selective PKC inhibitor, (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione hydrochloride salt.

12 Claims, No Drawings

THERAPEUTIC TREATMENT FOR CYTOMEGALOVIRUS INFECTION

This application claims the benefit of co-pending provisional application Ser. No. 60/076,857, filed Mar. 5, 1998, which is incorporated by reference herein.

BACKGROUND OF THE INVENTION

1. Field of the Invention

The present invention is broadly directed to a method for inhibiting activation of cytomegalovirus (CMV), especially reactivation of latent CMV. The present invention is particularly directed to the use of a particular class of isozyme selective Protein Kinase C (PKC) inhibitors for treating CMV infection and disease conditions associated with CMV infection, e.g., CMV mononucleosis and CMV syndromes in immunocompromised hosts.

2. Description of Related Art

CMV, which was initially isolated from patients with congenital cytomegalic inclusion disease, is now recognized as an important pathogen in all age groups. In addition to inducing severe birth defects, CMV causes a wide spectrum of disorders in older children and adults, ranging from an asymptomatic, subclinical infections to a mononucleosis syndrome in healthy individuals and to disseminated diseases in the immunocompromised. Human CMV is one of several related species-specific viruses that cause similar diseases in various animals. All are associated with the production of characteristic enlarged cells.

CMV has a worldwide distribution. Approximately 1 percent of newborns in the United States are infected with CMV, and the percentage is higher in many less-developed countries. Once infected, an individual probably carries the virus for life. Most commonly these infections remain latent. However, with a compromise of T-lymphocyte-mediated immunity, as occurs following organ transplantation or in association with lymphoid neoplasms and certain acquired immunodeficiencies, CMV reactivation syndromes develop frequently.

No specific and/or effective therapy is available for CMV infections. Treatment of ongoing CMV syndromes has been largely unsuccessful to date in transplant recipients and in patients with AIDS. Interferons, vidarabine, and acyclovir have failed, whether used alone or in combination. Newer nucleoside derivatives, such as 9-(1,3-dihydroxy-2-propoxymethyl) guanine (DHPG), have shown considerable activity against CMV in vitro. DHPG also shows promise in early clinical trials against CMV retinitis, colitis, and pneumonitis.

As one can appreciate, the presently available treatments for CMV infection and syndromes are scarce and not yet completely effective. There remains a need in the art to develop more ways to treat CMV infection and syndromes.

SUMMARY OF INVENTION

It is an object of the invention to provide a method for inhibiting CMV activation.

It is another object of the invention to provide a method for inhibiting CMV major immediate early gene activity.

It is yet another object of the invention to provide a method for treating CMV infection.

It is still another object of the invention to provide a method for treating CMV induced syndromes.

These and other objects of the invention are provided by one or more of the embodiments provided below.

In one embodiment of the invention there is provided a method for inhibiting activation of CMV which comprises administering to a mammal in need of such treatment a therapeutically effective amount of a particular class of protein kinase C inhibitors.

In another embodiment of the invention there is provided a method for inhibiting CMV major immediate early gene activity which comprises administering to a mammal in need of such treatment a therapeutically effective amount of a particular class of protein kinase C inhibitors.

In yet another embodiment of the invention there is provided a method for treating CMV infection which comprises administering to a mammal in need of such treatment a therapeutically effective amount of the protein kinase C inhibitor.

In still another embodiment of the invention there is provided a method for treating CMV induced syndromes which comprises administering to a mammal in need of such treatment a therapeutically effective amount of the protein kinase C inhibitor.

The present invention identifies compounds which are effective in treating CMV infection and disease conditions associated therewith, e.g.,CMV mononucleosis and CMV syndromes in immunocompromised hosts.

DETAILED DESCRIPTION OF THE INVENTION

It is a discovery of the present invention that the therapeutic use of a particular class of protein kinase C inhibitors, i.e., inhibitors of the β isozyme of protein kinase C, and especially β isozyme selective inhibitors of PKC, inhibits CMV major immediate early gene activity and CMV activation, especially latent CMV activation. Consequently, such compounds can be used therapeutically to treat CMV infection and disease conditions associated with CMV infection, e.g., CMV mononucleosis and CMV syndromes in immunocompromised hosts.

The compounds of the present invention are selective to protein kinase C over other kinases and are, quite surprisingly, highly isozyme selective. The term "isozyme selective" means the preferential inhibition of protein kinase C beta isozyme over protein kinase C isozymes, alpha, gamma, delta, epsilon, zeta, and eta.

The method of this invention preferably utilizes those protein kinase C inhibitors that effectively inhibit the β isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,552,396, 5,545,636, 5,481,003, 5,491,242, and 5,057,614, all incorporated by reference herein. Macrocyclic bis-indolylmaleimides are particularly represented by the compounds of formula I. These compounds, and methods for their preparation, have been disclosed in U.S. Pat. No. 5,552,396, which is incorporated herein by reference. These compounds are administered in a therapeutically effective amount to a mammal, e.g., human, to inhibit CMV major immediate early gene activity and CMV activation, e.g., latent CMV activation, or to treat CMV infection and CMV syndromes associated with CMV infection. These compounds can also be administered to patients at risk of the disease conditions mentioned above as prophylactics.

One preferred class of compounds for use in the method of the invention has the formula (I):

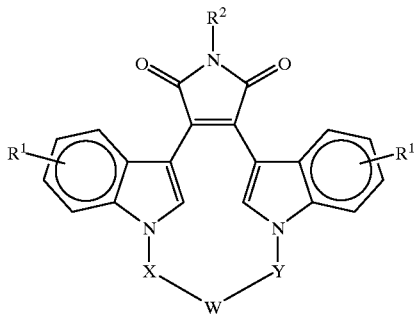

(I)

wherein:

W is —O—, —S—, —SO—, —SO₂—, —CO—, C₂-C₆ alkylene, substituted alkylene, C₂-C₆ alkenylene, -aryl-, -aryl(CH₂)ₘO—, -heterocycle-, -heterocycle-(CH₂)ₘO—, -fused bicyclic-, -fused bicyclic-(CH₂)ₘO—, —NR³—, —NOR³—, —CONH—, or —NHCO—;

X and Y are independently $C_1$-$C_4$ alkylene, substituted alkylene, or together X, Y, and W combine to form —(CH₂)ₙ—AA—;

$R^1$s are hydrogen or up to four optional substituents independently selected from halo, $C_1$-$C_4$ alkyl, hydroxy, $C_1$-$C_4$ alkoxy, haloalkyl, nitro, —NR⁴R⁵, or —NHCO($C_1$-$C_4$ alkyl);

$R^2$ is hydrogen, CH₃CO—, —NH₂, or hydroxy;

$R^3$ is hydrogen, —(CH₂)ₘaryl, —$C_1$-$C_4$ alkyl, —COO ($C_1$-$C_4$ alkyl), —CONR⁴R⁵, —(C=NH)NH₂, —SO ($C_1$-$C_4$ alkyl), —SO₂ (NR⁴R⁵), or —SO₂ ($C_1$-$C_4$ alkyl);

$R^4$ and $R^5$ are independently hydrogen, $C_1$-$C_4$ alkyl, phenyl, benzyl, or combine with the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof.

A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein $R^1$ and $R^2$ are hydrogen; and W is a substituted alkylene, —O—, S—, —CONH—, —NHCO— or —NR³—. Particularly preferred compounds for use in the invention are compounds of the formula Ia:

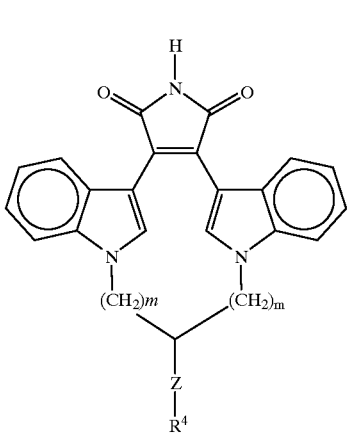

(Ia)

wherein Z is —(CH₂)ₚ— or —(CH₂)ₚ—O—(CH₂)ₚ—; $R^4$ is hydroxy, —SH, $C_1$-$C_4$ alkyl, (CH₂)ₘaryl, —NH(aryl), —N(CH₃)(CF₃), —NH(CF₃), or —NR⁵R⁶; $R^5$ is hydrogen or $C_1$-$C_4$ alkyl; $R^6$ is hydrogen, $C_1$-$C_4$ alkyl or benzyl; p is 0, 1, or 2; and m is independently 2 or 3, or a pharmaceutically acceptable salt, prodrug or ester thereof. Most preferred compounds of the formula Ia are those wherein Z is CH₂; and $R^4$ is —NH₂, —NH(CF₃), or —N(CH₃)₂, or a pharmaceutically acceptable salt, prodrug or ester thereof.

Other preferred compounds for use in the method of the present invention are compounds wherein W in formula I is —O—, Y is a substituted alkylene, and X is an alkylene. These preferred compounds are represented by formula Ib:

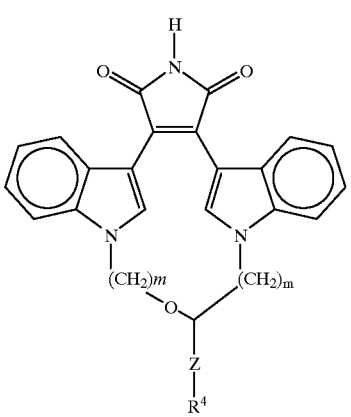

(Ib)

wherein Z is —(CH₂)ₚ—; $R^4$ is —NR⁵R⁶, —NH(CF)₃, or —N(CH)₃(CF)₂; $R^5$ and $R^6$ are independently H or $C_1$-$C_4$ alkyl; p is 0, 1, or 2; and m is independently 2 or 3, or a pharmaceutically acceptable salt, prodrug or ester thereof. Most preferred compounds of formula Ib are those wherein p is 1; and $R^5$ and $R^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985).

The synthesis of various bis-indole-N-maleimide derivatives is described in Davis et al. U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference.

One particularly preferred protein kinase-β inhibitor for use in the method of this invention is the compound described in Example 5 g ((S)-3,4-[N,N'-1,1'-((2"-ethoxy)-3'"(O)-4'"-(N,N-dimethylamino)-butane)-bis-(3,3'-indoly1)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta-2 isozymes. Other salts of this compound also would be favored, especially the mesylate salts, as described in U.S. Pat. No. 5,710,145 (incorporated herein by reference).

A preferred mesylate salt can be prepared by reacting a compound of the formula II:

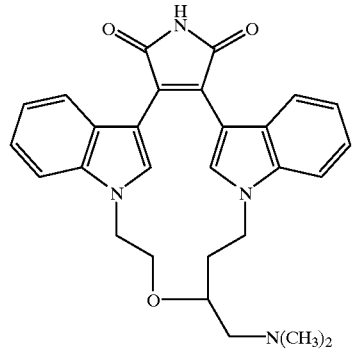

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration or other separation techniques appreciated in the art, directly from the reaction mixture in yields ranging from 50% to 100%. Recrystallization and other purification techniques known in the art may be used to purify the salt further if desired.

The inhibitors of the β isozyme of PKC described in the present invention can be used to inhibit CMV activation including reactivation of latent CMV. CMV is a member of the herpesvirus group and contains double-stranded DNA, a protein capsid, and a lipoprotein envelope. CMV replicates in the cell nucleus, and can cause either a lytic and productive or a latent infection. Often CMV infection results from reactivation of latent CMV that is harbored in monocytes, stem cells, and T cells.

CMV activation comprises the states of productive infection and reactivation of latent infection. CMV activation includes replication of CMV genome, expression of CMV genes, virus assembling, as well as releasing infectious CMV particles and CMV proteins. CMV replication includes production of multiple copies of CMV genome and integrated latent CMV genome. CMV expression includes production of viral proteins, e.g., major immediate early (MIE) gene products.

CMV reactivation can be regulated by several factors including MIE gene products and regulating factors thereof. MIE genes usually contain promoters with responsive sites. Positive responsive sites, e.g., AP-1, NF-kB, cyclic AMP, serum response factor and overlapping serum response factor/ELK-1 sites may be activated by protein kinase C. Gene expression of MIE could also be responsive to the differentiation or activation state of monocytes. Differentiation of monoblastoid cells into more mature monocyte/macrophage-like cells is associated with an increase in the cellular content of the protein kinase C-β isoform.

Though not wishing to be limited to any technical explanation, applicants believe that under conditions in which protein kinase C-β content is elevated or protein kinase C is activated, MIE gene products are expressed and activation or reactivation of latent cytomegalovirus infection occurs in monocytes and T cells. Therefore, administration of a protein kinase C inhibitor would inhibit MIE gene activity and CMV activation, especially reactivation of latent CMV infection.

The inhibitors of the β isozyme of PKC described in the present invention can be used to treat CMV infection and the disease conditions associated therewith, especially a variety of CMV syndromes in immunocompromised hosts.

Congenital CMV infection follow either primary or reactivation infection of the mother. However, clinical disease in the fetus or newborn is almost exclusively limited to infants born to mothers who develop primary infections during pregnancy. Fetal infections range from inapparent to severe and disseminated. Petechiae, hepatosplenomegaly, and jaundice are the most common presenting features. Microcephaly with or without cerebral calcifications, intrauterine growth retardation, and prematurity are noted in 30 to 50 percent of patients.

Primary infection in late childhood or adulthood is often associated with a vigorous T-lymphocyte response that may contribute to the development of a mononucleosis syndrome similar to that observed following Epstein-Barr virus infection. The most common clinical manifestation of CMV infection in normal hosts beyond the neonatal period is a heterophil-antibody negative mononucleosis syndrome. This may occur spontaneously or following the transfusion of leukocyte-containing blood products. Although the syndrome occurs at all ages, sexually active young adults are most often involved. Prolonged high fevers, sometimes accompanied by chills, profound fatigue, and malaise characterize this disorder.

Once acquired during symptomatic or asymptomatic primary infection, CMV persists indefinitely in tissues of the host. If T-cell responses of the host become compromised by disease or by iatrogenic immunosuppression, latent virus can be reactivated to cause a variety of syndromes. Chronic antigenic stimulation, as occurs following tissue transplantation, in the presence of immunosuppression, appears to be an ideal setting for CMV activation and CMV-induced disease conditions. CMV may itself contribute to further T-lymphocyte hyporesponsiveness which often precedes superinfection with other opportunistic pathogens.

CMV appears to be the most frequent and important viral pathogen complicating organ transplantation. In renal, cardiac, and liver transplant recipients, CMV induces a variety of syndromes including fever and leukopenia, hepatitis, pneumonitis, colitis, and retinitis. CMV syndromes in the immunocompromised host often begin with prolonged fever, malaise, anorexia, fatigue, night sweats, and arthralgias or myalgias.

CMV is also recognized as an important pathogen in patients with the acquired immunodeficiency syndrome (AIDS). CMV infection is nearly ubiquitous in this disorder and often causes disseminated disease, contributing to death.

One skilled in the art will recognize that a therapeutically effective amount of the protein kinase C inhibitor of the present invention is the amount sufficient to inhibit MIE gene activity and CMV activation including reactivation of latent CMV infection. Such amount varies inter alia, depending upon the concentration of the compound in the therapeutic formulation, the body weight of the patient, the condition of the patient and the method of application.

Generally, an amount of protein kinase C inhibitor to be administered as a therapeutic agent will be determined on a case by case basis by the attending physician. As a guideline, the degree of CMV infection, the degree of syndromes derived from CMV infection, the duration of CMV infection, the association with other diseases, e.g., transplantation and AIDS, the body weight and the age of a patient, the mode of administration, and the like will be considered when setting an appropriate dose. Some other factors to be considered as reference are the patients hypertension, smoking habit, and overall vascular condition.

Generally, a suitable dose is one that results in a concentration of the protein kinase C inhibitor at the treatment site in the range of 0.5 nM to 200 $\mu$M, and more usually between about 0.5 nM to 200 nM. It is expected that serum concentrations of 0.5 nM to 20 nM should be sufficient in many circumstances.

To obtain these treatment concentrations, a patient in need of treatment likely will be administered between about 0.001 mg per day per kg of body weight and 50.0 mg per day per kg. Usually, not more than about 10.0 mg per day per kg of body weight of protein kinase C inhibitor should be needed. As noted above, the above amounts may vary on a case-by-case basis.

The therapeutic effects of the methods in the present invention can be evaluated by examining the effects of the PKC isozyme selective inhibitors on monoblastoid cells. Specifically, the effects of the compounds of formula I and the preferred compounds of formula Ia and Ib on the differentiation or activation of monoblastoid cells, e.g. U937 could be examined. For example, U937 monoblastoid cells can be treated with phorbol esters or any other activator to stimulate monocytic differentiation and/or activation. An inhibition or blockage of monoblastoid cell differentiation or activation is predictive of a positive response in preventing or inhibiting CMV activation including reactivation of latent CMV infection.

The effects of the compounds on CMV activation and infection could also be determined by transient transfection. T cell or monoblastoid cell lines can be transiently transfected with a MIE promoter-reporter construct. The transfected cells will be incubated with either placebo or a differentiation/activation activator, e.g., phorbol esters in the absence or presence of a protein kinase C-β selective inhibitor. An inhibition or blockage of the reporter gene activity induced by the activator is predicative of a positive response in abrogating MIE gene activity.

The effects of the compounds on CMV activation and infection could also be assessed by measuring the ability of the compound in in vitro infected cells. Monoblastoid cells could be infected with CMV in the presence of an differentiation/activation activator, e.g., phorbol esters. Subsequently, the infected cells would be incubated with either placebo or a protein kinase C-β inhibitor. A decrease in MIE mRNA transcripts in the infected cells or in the production of progeny virions is predictive of a positive response in inhibiting MIE gene activity, CMV activation and CMV infection.

The compounds of formula I, and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 5–15 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels. In a preferred embodiment, intracavernosal injection of the compound directly to the smooth muscle is used.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon concentration of compound in the formulation. Generally, the formulation will be applied to the effected tissue in an amount affording from about 1 to about 500 $\mu$g compound per $cm^2$ of an affected tissue. Preferably, the applied amount of compound will range from about 30 to about 300 $\mu g/cm^2$, more preferably, from about 50 to about 200 $\mu g/cm^2$, and, most preferably, from about 60 to about 100 $\mu g/cm^2$.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active agent | 5 |
| starch, dried | 200 |
| magnesium stearate | 10 |
| Total | 215 mg |

The above ingredients are mixed and filled into hard gelatin capsules in 460 mg quantities.

Formulation 2

A tablet is prepared using the ingredients below:

|  | Quantity (mg/capsule) |
| --- | --- |
| Active agent | 15 |
| cellulose, microcrystalline | 10 |
| silicon dioxide, fumed | 10 |
| stearic acid | 5 |
| Total | 40 mg |

The components are blended and compressed to form tablets each weighing 665 mg.

Formulation 3

Tablets each containing 60 mg of active ingredient are made as follows:

|  | Quantity (mg/tablet) |
| --- | --- |
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

What is claimed is:

1. A method for inhibiting cytomegalovirus activation which comprises administering to a mammal in need of such treatment, a therapeutically effective amount of a β isozyme selective protein kinase inhibitor wherein the β isozyme selective protein kinase C inhibitor is a bis-indolylmaleimide or a macrocyclic bis-indolylmaleimide.

2. The method of claim 1 wherein the beta-isozyme selective protein kinase C inhibitor has a selectivity which is selected from the group consisting of β-1 isozyme selectivity and beta-2 isozyme selectivity.

3. The method of claim 2 wherein the protein kinase C inhibitor has the following formula:

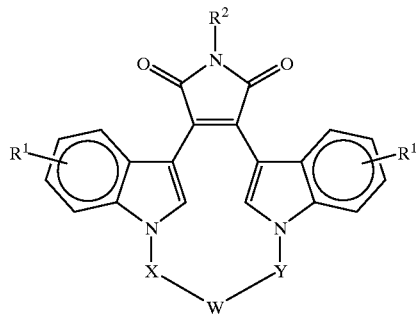

(I)

wherein:

W is —O—, —S—, —SO—, —SO$_2$—, —CO—, C$_2$–C$_6$ alkylene, substituted alkylene, C$_2$–C$_6$ alkenylene, —aryl—, —aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy;

R$^3$ is hydrogen, —(CH$_2$)$_m$aryl, —C$_1$–C$_4$ alkyl, —COO (C$_1$–C$_4$ alkyl), —CONR$^4$R$^5$, —(C=NH)NH$_2$, —SO (C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

4. The method of claim 3 wherein the protein kinase C inhibitor has the following formula:

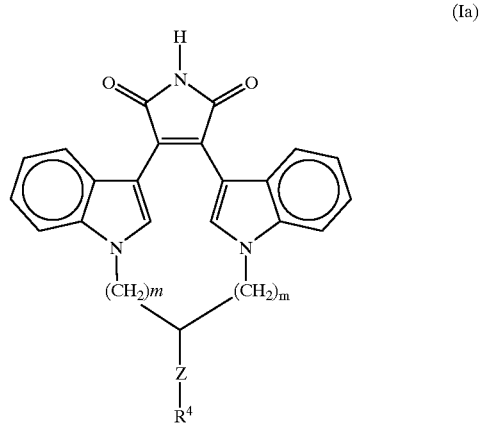

(Ia)

wherein Z is —(CH$_2$)$_p$— or —(CH$_2$)$_p$—O—(CH$_2$)$_p$—; R$^4$ is hydroxy, —SH, C$_1$-C$_4$ alkyl, (CH$_2$)$_m$aryl, —NH (aryl), —N(CH$_3$) (CF$_3$), —NH(CF$_3$), or —NR$^5$R$^6$; R$^5$ is hydrogen or C$_1$-C$_4$ alkyl; R$^6$ is hydrogen, C$_1$-C$_4$ alkyl or benzyl; p is 0, 1, or 2; and m is independently 2 or 3, or a pharmaceutically acceptable salt, prodrug or ester thereof.

5. The method of claim 3 wherein the protein kinase C inhibitor has the following formula

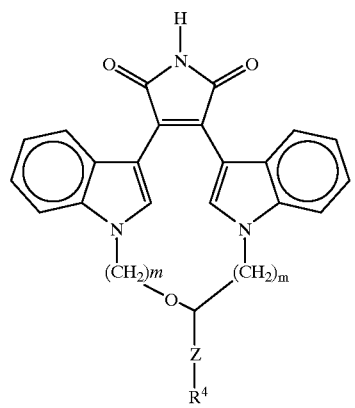

(Ib)

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or C$_1$-C$_4$ alkyl; p is 0, 1, or 2; and m is independently 2 or 3, or a pharmaceutically acceptable salt, prodrug or ester thereof.

6. The method of claim 3, wherein the protein kinase C inhibitor comprises (S)-3,4-[N,N'-1,1'-((2"-ethoxy)-3'''(O)-4'''-(N,N-dimethylamino)-butane)-bis-(3,3'-indolyl)]-1(H)-pyrrole-2,5-dione or its pharmaceutically acceptable acid salt.

7. A method for inhibiting cytomegalovirus activation which comprises administering to a mammal in need of such treatment, a therapeutically effective amount of a β isozyme selective protein kinase C inhibitor, said β isozyme selective protein kinase C inhibitor comprising a compound of the formula:

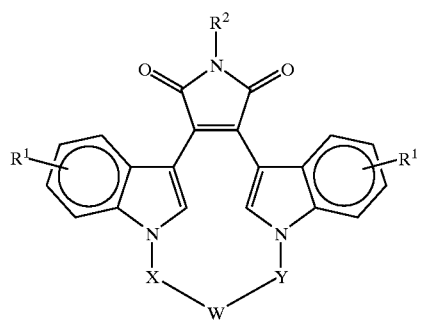

(I)

wherein:
W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$-C$_4$ alkylene, substituted alkylene, or together X, Y, and W combine to form —(CH$_2$)$_n$—AA—;

R$^1$s are hydrogen or up to four optional substituents independently selected from halo, C$_1$-C$_4$ alkyl, hydroxy, C$_1$-C$_4$ alkoxy, haloalkyl, nitro, NR$^4$R$^5$, or —NHCO(C$_1$-C$_4$ alkyl);

R$^2$ is hydrogen, CH$_3$CO—, NH$_2$, or hydroxy;

R$^3$ is hydrogen, —(CH$_2$)$_m$aryl, —C$_1$-C$_4$ alkyl, —COO (C$_1$-C$_4$ alkyl), —CONR$^4$R$^5$, —(C=NH)NH$_2$, —SO (C$_1$-C$_4$ alkyl), —SO$_2$ (NR$^4$R$^5$), or —SO$_2$(C$_1$-C$_4$ alkyl);

R$^4$ and R$^5$ are independently hydrogen, C$_1$-C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

8. The method of claim 7 wherein the β-isozyme selective protein kinase C inhibitor has a selectivity which is selected from the group consisting of beta-1 isozyme selectivity and beta-2 isozyme selectivity.

9. The method of claim 8 wherein the β-isozyme selective protein kinase C inhibitor has the following formula:

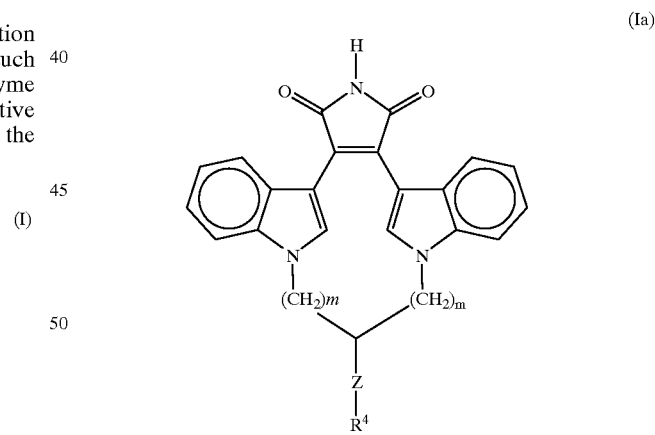

(Ia)

wherein Z is —(CH$_2$)$_p$— or —(CH$_2$)$_p$—O—(CH$_2$)$_p$—; R$^4$ is hydroxy, —SH, C$_1$-C$_4$ alkyl, (CH$_2$)$_m$aryl, —NH (aryl), —N(CH$_3$) (CF$_3$), —NH(CF$_3$), or —NR$^5$R$^6$; R$^5$ is hydrogen or C$_1$-C$_4$ alkyl; R$^6$ is hydrogen, C$_1$-C$_4$ alkyl or benzyl; p is 0, 1, or 2; and m is independently 2 or 3, or a pharmaceutically acceptable salt, prodrug or ester thereof.

10. The method of claim 8 wherein the β-isozyme selective protein kinase C inhibitor has the following formula:

(Ib)

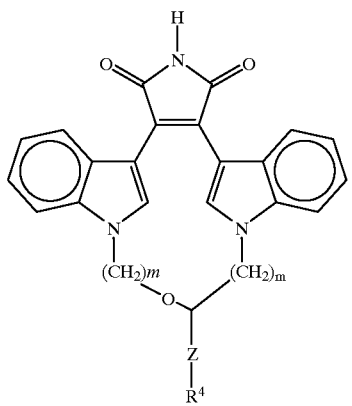

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof.

11. The method of claim 8, wherein the β-isozyme selective protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

12. A method for inhibiting cytomegalovirus major immediate early gene activity which comprises administering to a mammal in need of such treatment, a therapeutically effective amount of a β-isozyme selective protein kinase C inhibitor, said β isozyme selective protein kinase C inhibitor comprising a compound of the formula:

(II)

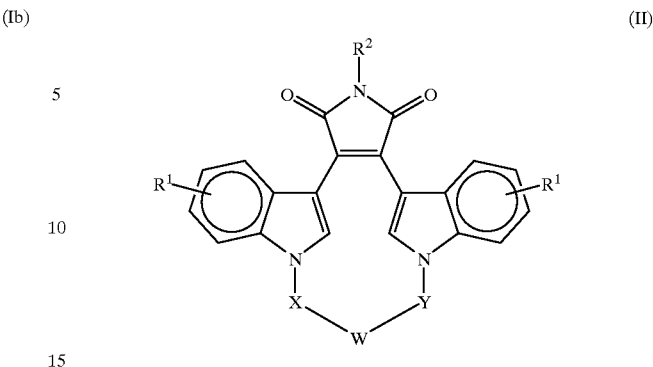

wherein:
  W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;
  X and Y are independently C$_1$–C$_4$ alkylene, substituted alkylene, or together X, Y, and W combine to form —(CH$_2$)$_n$—AA—;
  R$^1$'s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);
  R$^2$ is hydrogen, CH$_3$CO—, NH$_2$, or hydroxy;
  R$^3$ is hydrogen, —(CH$_2$)$_m$aryl, —C$_1$–C$_4$ alkyl, —COO (C$_1$–C$_4$ alkyl), —CONR$^4$R$^5$, —(C=NH)NH$_2$, —SO (C$_1$–C$_4$ alkyl), —SO$_2$ (NR$^4$R$^5$), or —SO$_2$ (C$_1$–C$_4$ alkyl);
  R$^4$ and R$^5$ are independently hydrogen, C$_1$–C$_4$ alkyl, phenyl, benzyl, or combine to the nitrogen to which they are bonded to form a saturated or unsaturated 5 or 6 member ring;
  AA is an amino acid residue;
  m is independently 0, 1, 2, or 3; and
  n is independently 2, 3, 4, or 5
or a pharmaceutically acceptable salt, prodrug or ester thereof.

* * * * *